United States Patent [19]

Reichle

[11] 4,086,188
[45] Apr. 25, 1978

[54] CATALYST FOR ALDOL CONDENSATIONS

[75] Inventor: Walter Thomas Reichle, Millington, N.J.

[73] Assignee: Union Carbide Corporation, New York, N.Y.

[21] Appl. No.: 745,809

[22] Filed: Nov. 29, 1976

Related U.S. Application Data

[63] Continuation-in-part of Ser. No. 657,568, Feb. 12, 1976, abandoned.

[51] Int. Cl.² .................... B01J 21/04; B01J 21/10; B01J 23/02; B01J 23/04
[52] U.S. Cl. ............................ 252/463; 260/586 C
[58] Field of Search .................... 252/463; 260/586 C

[56] References Cited

U.S. PATENT DOCUMENTS 3,337,633  8/1967  Schmitt et al. .................. 260/586 C

*Primary Examiner*—W. J. Shine
*Attorney, Agent, or Firm*—Bernard Francis Crowe

[57] ABSTRACT

Aldol condensation catalysts have been prepared by interacting stoichiometric amounts of a water soluble salt of a Group II metal and a water soluble aluminum salt with a stoichiometric amount of an alkaline metal or alkaline earth metal, water soluble hydroxide and doping the washed slurry which precipitates with a water soluble lithium or zinc salt.

23 Claims, 1 Drawing Figure

MESITYL OXIDE / ISOPHORONE WEIGHT RATIO
VS.
TOTAL ACETONE CONVERSION
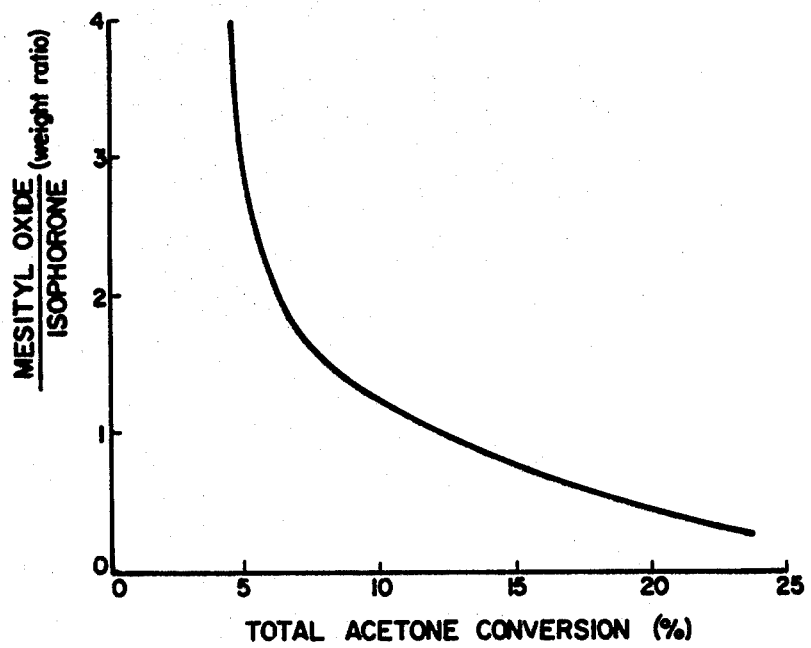

CATALYST FOR ALDOL CONDENSATIONS

This is a continuation-in-part of Ser. No. 657,568 filed Feb. 12, 1976, now abandoned.

BACKGROUND OF THE INVENTION

This invention pertains to aldol condensations and more particularly to the heterogeneous catalyst used for said aldol condensations.

The aldol condensation of active hydrogen containing organic carbonyl compounds has been widely used in industry for synthesize compounds. Base catalyst such as alkali metal hydroxides have been used for producing 2-ethylhexanediol-1,3, 2-ethylhexanol-1, diacetone alcohol, isophorone, mesityl oxide, methyl isoamyl ketone, methyl isobutyl ketone, and the like.

Myriad methods have been disclosed for converting, for example, acetone by aldol condensation into a variety of products particularly isophorone and mesityl oxide which are used in industrial solvents and as chemical intermediates for resins, dyes, insecticides and the like. By-products which arise from the general reaction include diacetone alcohol, 4,4-dimethyl-hepta-2,6-dione, 4,6-dimethyl-hepta-3,5-diene-2-one, 3,5,5-trimethylcyclohex-3-ene-one, mesitylene, 2,2,6,6-tetramethyl, tetrahydropyran-4-one, xylitones, and isoxylitones, as well as various unidentified high boilers and tars. Needless to say, the specificity of the reaction must be controlled for commercial success in order to direct the conversion of acetone to the desired end products.

It is an object of this invention to control the condensation of acetone to produce chiefly mesityl oxide and isophorone and in addition to limit the molar ratio of mesityl oxide:isophorone produced to a low value (preferably less than 1) to conform to the commercial demand for these 2 products.

It is another object of the invention to provide a catalyst for this control condensation of acetone having the following properties:
High and constant activity
Reproducible activity
Long Catalyst Life
Ability to regenerate readily
Consistent in selective production of mainly mesityl oxide and isophorone
Cheap and available Examples of typical catalysts used for the conversion of acetone to isophorone and mesityl oxide are: alkali metal hydroxides, such as, sodium, potassium, and lithium hydroxide; alkaline earth hydroxides, such as, calcium, magnesium, strontium and barium hydroxide; calcium aluminate, sodium aluminate, calcium borate, potassium zincate, magnesium plumbate, barium aluminate, lithium plumbate, sodium borate, strontium stannate, potassium stannate, calcium borate, magnesium antimonate, sodium antimonate, calcium arsenate, sodium arsenate, potassium titanate, calcium zincate, magnesium aluminate, beryllium aluminate, cesium borate, rubidium arsonate, lithium phosphate, magnesium oxide, and the like.

It is another object of this invention to provide a catalyst and method for the aldol condensation of active hydrogen containing organic carbonyl compounds in general.

SUMMARY OF THE INVENTION

An improved catalyst for the aldol condensation of active hydrogen containing organic carbonyl compounds has been developed by the steps of:
(a) interacting stoichiometric amounts of a water-soluble salt of a metal of Group II of the Deming Periodic Table and a water-soluble aluminum salt with a stoichiometric amount of an alkali metal or alkaline earth metal, water-soluble hydroxide in water to precipitate a water-insoluble slurry of mixed hydroxides with the proviso that the ratio of gram atoms of Group II metal to aluminum metal is in the range of about 0.02 to about 0.3;
(b) washing the slurry from step (s) with water until substantially free of water-soluble salts;
(c) contacting the washed slurry from step (b) with a dilute aqueous solution of a lithium or zinc salt at ambient temperatures; and
(d) recovering and drying the product of step (c) at a temperature below about 400° C.

A catalyst which is unusually active and selective in the ratio of condensation products obtained has been developed in a series of steps comprising:
(a) interacting a stoichiometric amount of a water-soluble salt of a metal of Group II of the Deming Periodic Table with a stoichiometric amount of an inorganic water-soluble hydroxide in water to precipitate a water-insoluble slurry;
(b) mixing 100 parts by weight on a dry basis of the slurry of step (a) with about 1 to about 20 parts by weight, of a water-soluble salt of a metal of Group II of the Deming Periodic Table dissolved in water to produce a second slurry;
(c) mixing 100 parts by weight on a dry basis of the slurry of step (b) with about 2 to about 40 parts by weight on a dry basis of an alkali metal aluminate to afford a third slurry;
(d) washing the slurry of step (c) with water until substantially free of the water-soluble salts;
(e) contacting the washed slurry of step (d) with a dilute aqueous solution of a lithium or zinc salt at ambient temperatures; and
(f) recovering and drying the product of step (e) at a temperature below about 400° C.

Exemplary water-soluble salts of metals of Group II of the Deming Periodic Table include nitrates, halides, acetates, and the like, of beryllium, magnesium, calcium, strontium, barium, zinc and cadmium.

Representative inorganic water-soluble hydroxides which can be used include: alkali metal hydroxides, such as, sodium hydroxide, potassium hydroxide, lithium hydroxide, rubidium hydroxide and caesium hydroxide; alkaline earth metal hydroxides, as for example, calcium hydroxide, strontium hydroxide, barium hydroxide, and the like.

Suitable lithium and zinc salts which can be used for doping the slurry obtained in step (d) above include halides (i.e., the fluorides, chlorides, bromides and iodides), the nitrates, sulfates, perchlorates, acetates, and the like. The term "dilute aqueous solutions" of the above-mentioned salts is meant to mean salt concentrations between about 0.1 and about 100 grams of salt per liter of water.

It is preferred that sufficient "dilute aqueous solution" be used in step (e) to afford recovering a slurry from step (e) wherein 100 parts by weight of said slurry contains about 1.0 to about 0.001 parts by weight of lithium or zinc ion.

It is preferred that the mole ratio of the Group II metal salt, in step (b), to the alkali metal aluminate in step (c) be about 1:2 ± 10 mole % and that the slurry in step (d) contains 80 to 99% by weight of the precipitate from step (a) and 1 to 20% by weight of the slurry from step (c).

The catalyst described in the preceding paragraph cannot be delineated by a simple formula since the chemical nature and identity of the products obtained in each one of the steps cannot be rigorously identified. In one preferred form the catalyst is prepared by first interacting in step (a) a stoichiometric amount of a water-soluble magnesium salt, such as, magnesium nitrate dissolved in water with a stoichiometric amount of sodium hydroxide in water. A simplistic view of this reaction would involve the interaction of one mole of magnesium nitrate with 2 mols of sodium hydroxide in water to produce 1 mole of "magnesium hydroxide" precipitate and 2 mols of sodium nitrate. However, the precipitate is believed to comprise a complex of magnesium oxides and hydroxides and not solely $Mg(OH)_2$.

In the next step of the preferred catalyst preparation, additional magnesium nitrate as an aqueous solution is mixed the slurry from step (a) forming a second slurry followed by the treatment of this slurry with sodium aluminate. The slurry arising at this step is even more complex containing probably some form of magnesium-aluminum hydroxides and oxides. The washing of this slurry removes any residual water-soluble salts, such as, magnesium nitrate and sodium nitrate. This slurry when treated with a water-soluble lithium salt, such as, lithium chloride has the effect of doping or modifying the complex mixture of magnesium-aluminum hydroxides and oxides in an unknown manner. When isolated and dried however this product is found to exhibit catalytic properties startlingly superior to the material from step (d) which contains no lithium ion. X-ray analysis of this lithium doped product reveals an amorphous structure clearly demonstrating that the product is not a crystalline product, such as, magnesium aluminate or its naturally occurring mineral counterpart, "spinel". While it is not clear what the exact morphology of this catalyst is, the lithium ions present are chemically bound and not merely agglomerated since they remain in the catalyst after the water washing. While not wishing to be bound by any theory or scientific explanation, it is submitted that the lithium undergoes some type of ion exchange reaction with the surface of the complex of magnesium-aluminum hydroxides and oxides.

Zinc ion is also effective for the doping of the magnesium-aluminum hydroxides and oxides complex in place of lithium ion. Again, the mechanism of the unexpected advantages accompanying this doping operation is not known. However, as in the case of lithium, it is also speculated that some type of ion exchange reaction takes place since the zinc ions are not removed by a washing step.

The catalysts of this invention are also characterized by the following physical properties: a pore volume of about 0.20 to about 0.50 cc./g., preferably about 0.32 to 0.36 cc./g., a surface area of about 20 to about 400 meters$^2$/g., preferably about 50 to 100 meters$^2$/g., and a bulk density of about 0.70 to about 0.90 cc./g., preferably about 0.8 to 0.9 cc./g. Another distinction between the catalysts of this invention and those of the prior art lies in the fact that the instant catalysts are not subjected in their preparation of temperatures of above about 400° C. which is generally the case for the preparation of compounds such as magnesium-aluminate (spinel). The latter are used in the electronic industry as insulators or semi-conductors.

The commercial demand for mesityl oxide and isophorone makes it desirable that the product ratio of mesityl oxide to isophorone be less than about 1 otherwise excess mesityl oxide has to be recycled to the operating unit. Conventional catalysts presently in use, such as, calcium hydroxide produce mesityl oxide:isophorone ratios of two to about five which is undesirable from an economic standpoint. The catalysts of this invention as shown in the FIGURE afford these desirable mesityl oxide:isophorone weight ratios at reasonable acetone conversion levels. This product ratio can also be modified by merely adjusting the acetone conversion.

Another unexpected property of the catalysts of this invention is the fact that while water depresses the reaction rate somewhat it also increases the reaction efficiency of converting acetone to isophorone and mesityl oxide which suppressing the formation of undesirable by-products.

The preferred temperature range for converting acetone to mesityl oxide and isophorone using the catalysts of this invention lies in the range of about 250° to about 350° C. with a more preferred range lying in the range of about 280° to about 320° C.

Pressure is not narrowly critical but pressures of about 1 to about 5 atmospheres are preferred. If desired the conversion of acetone with the catalysts of this invention can be effected at atmospheric and below as well as higher superatmospheric pressures.

The feed rate of acetone is not narrowly critical but it is preferred for efficient operations to range between about 20 and 140 pounds of acetone per/hour/foot$^3$ of catalyst. This corresponds to an hourly vapor space velocity of about 90 to about 700 cubic feet of gaseous acetone per cubic foot of catalyst per hour. At about 300° C. and 3 atmospheres, the preferred contact time is about 5 to about 40 seconds.

It is preferred to hold percent conversion of acetone in the range of about 7 to about 30 percent by weight.

The life of the catalysts of this invention is surprisingly long and is in excess of about 7000 hours for the efficient conversion of acetone. An unexpected attribute of these catalysts is the fact that their life can be extended further by regeneration consisting of heating the catalyst in the presence of air or oxygen at a temperature in the range of about 250° to 350° C. thereby burning off any adhering polymer and non-volatile by-products. Surprisingly the regenerated catalyst is as efficient and in many cases more efficient than the original catalyst.

The terms conversion and efficiency of the acetone conversion are used in this invention as defined below:

$$\text{Conversion} = 10^2 \times \frac{(A - B)}{(A)}$$

$$\text{Efficiency} = 10^2 \times \frac{(MSO + I)}{(A - B)}$$

Where:
A = Total Acetone equivalents fed
B = Total Acetone in product

MSO = Total Equivalents of acetone in the mesityl oxide product

I = Total equivalents of acetone in the isophorone product.

The term "Acetone Equivalent" is one for acetone, two for mesityl oxide and three for isophorone for purposes of this disclosure. It simply accounts for each mole of acetone fed to the reactor whether in reacted or unreacted form.

While the highest efficiencies are obtained by using an anhydrous acetone feed having a purity of 99 percent or greater, this invention can be used with acetone having a purity as low as about 70 percent by weight with the balance being mesityl oxide, water and other materials, such as, isopropanol, hexanes, and the like.

The conversion of acetone to mesityl oxide and isophorone according to this invention is preferably carried out over a fixed catalyst bed.

The catalysts of this invention do not require a support. They can be pelleted, extruded or shaped into any desired form. However, if desired they can also be formulated to be carried on an inert material.

The testing of these catalyst compositions was carried out by two methods. The first involved the use of a pulse reactor-gas chromatographic combination which yields rapid and semi-quantitative data. This was used principally as a screening tool to detect highly active catalysts for subsequent testing. Also the reaction chemistry and other features were examined by this technique. The second method was a one-inch i.d. pilot plant reactor. In this latter device long term testing was carried out.

The initial screening operations used in the discovery of this catalyst system were effected by means a pulse reactor consisting of a modified Hewlett-Packard Model 5750-B gas chromatograph. The gas chromatograph separation column was 10 feet long and $\frac{1}{8}$ inch in diameter packed with 20 percent Carbowax 20M (Trademark of Union Carbide Corporation for polyethylene glycol having a formula molecular weight range of about 18,000 to 19,000) on Chromosorb T (a polytetrafluoroethylene support sold by Johns-Manville Co.).

The programming schedule was 50° to 100° C. at 8°/min. Detection was by fid (flame ionization detection) although the less sensitive tc (thermal conductivity) mode can also be used. The detector temperature was 300° C. Peak integration was carried out by an electronic coulometer.

The injection port kept at 300° C. was $\frac{1}{4}$ inch i.d. into which a 2mm o.d. glass liner filled with catalyst (about 0.1 to 0.2 g.) was inserted. Specially cut silicone rubber septa prevented gases from by-passing this glass catalyst holder.

In the general procedure six 25 μliter fractions of acetone were initially injected into the catalyst bed. These injections were carried out in rapid succession; after this the catalyst in the separation column was cleared of all reaction products by sweeping helium through for about 2 hours. After this two 2 μliter injections of acetone were used to measure the initial catalyst activity.

The pilot plant reactor is described below:

ONE-INCH PILOT PLANT REACTOR

This device consists of a 1 inch i.d. pipe (300 cm long) made of 304 stainless steel. The bottom 165 cm contained about 1 liter of catalyst. A $\frac{1}{4}$ inch thermocouple well went through the center of this catalyst bed. In it were 6 thermocouples, equally spaced. Readings were a multipoint recorder. On each end of the catalyst bed was a glass wool plug (~7 cm) and a Carpenter 20 "Neva-Clog" screen. Before the catalyst bed was a 120 cm preheat section of $\frac{1}{4}$ inch glass balls. Acetone liquid was pumped with a reciprocating plunger pump into a tubular heat exchanger (2 ft.$^2$ surface area, steam heated, 190 psi) and then directly onto the glass bead section. Vapor flow was in a downward direction. Heating was by $\frac{3}{4}$ inch-high temperature glass fiber insulated tapes which were controlled by temperature controllers. The reactor pressure was controlled with appropriate valves. Following this was a 2 ft.$^2$ heat exchanger. Weights (in and out) were on 100 kg. balances (±25 g.). Usually the material balance was within 2%. Gas formation—invariably nil—could be checked with a wet test meter.

Data from this pilot plant reactor can be quantitatively related to plant scale operations.

ANALYTICAL METHODS

Water was determined by Karl Fischer titration or by using thermal conductivity detection. The reaction crudes were analyzed by gas chromatography. Area-wt. % correlations were established using synthetic known samples.

Typical pulse-reactor results are presented later. They were calculated from the pulse reactor-gas chromatographic runs carried out by the above procedure. Calcium hydroxide, a commonly using heterogeneous catalyst from acetone aldol condensations, was added as a reference but was relatively inactive.

The activity of each catalyst can be inferred from the recovered acetone percentage. The smaller this number the more acetone is converted, the more active the catalyst is.

The term "active hydrogen-containing organic compounds" as used herein includes those having the group $\geq$C—H adjacent to a aldehydic or ketonic carbonyl group, a nitro group, a cyano group and other electron withdrawing groups such as those present in quaternary salts.

Preferred active hydrogen containing organic carbonyl compounds which are susceptible to aldol condensation using the catalysts of this invention include aliphatic aldehydes, such as, formaldehyde in conjunction with other active hydrogen containing compounds, acetaldehyde, n-butyraldehyde and the like, aliphatic ketones such as methyl ethyl ketone, methyl isobutyl ketone, diethyl ketone, and the like, cycloaliphatic ketones, such as, cyclohexanone, as well as acetone.

The above described catalysts unexpectedly demonstrate selective reactivity even for such closely related aliphatic aldehydes as n-butyraldehyde and its isomer isobutyraldehyde. It was demonstrated that n-butyraldehyde reacted over 8 times faster than isobutyraldehyde in an aldol condensation using these catalysts.

The invention is further described in the examples which follow. All parts and percentages are by weight unless otherwise specified.

EXAMPLE 1

Lithium Ion Doped Catalyst Preparation

A solution of 1440 g. of magnesium nitrate, $Mg(NO_3)_2 \cdot 6H_2O$ in 8 liters of distilled water was charged to a stainless steel 5 gallon reactor equipped with a mechanical stirrer and addition funnel. A solution of 421 grams of sodium hydroxide, NaOH, in 4 liters of distilled water was then added dropwise over a period of about 4 hours with good stirring. The pH of the contents of the reactor was about 9 to 10. A white precipitate or slurry formed during this step. There was next added 50 grams of $Mg(NO_3)_2 \cdot 6H_2O$ to the slurry with continued stirring followed by the slow addition of a solution of 32.0 grams of $NaAlO_2$ in 1100 ml. of distilled water over a two hour period. The pH of the resultant slurry was about 8.

After standing overnight the slurry was filtered and the filter cake carefully washed three times with 1.5 liters of distilled water. The wet cake weighed 639.8 grams and had a solids content of 47.5% (determined on an aliquot portion dried at 100° C./30 mm. for 24 hours in a vacuum oven).

Fifty grams of the wet cake was doped with lithium ions by re-slurring, in a solution containing 0.5 grams of $LiNO_3$ dissolved in 500 ml. of distilled water, for four hours followed by filtration and drying of the filter cake in a vacuum oven at 100° C./30 mm. for 24 hours.

EXAMPLE 2

Zinc Ion Doped Catalyst Preparation

Example 1 was repeated with the exception that the doping step was carried out by re-slurrying 50.0 grams of the wek cake in a solution containing 1.0 grams of $Zn(NO_3)_2 \cdot 6H_2O$ for 4 hours followed by filtration and drying of the filter cake in a vacuum oven at 100° C./30 mm. for 24 hours.

EXAMPLE 3

Testing of Lithium and Zinc Ion Doped Catalysts

The pulse-gas chromatographic technique described supra was used for testing the catalysts prepared as in Examples 1 and 2 and compared with a Control A which was identical to the Example 1 catalyst except that no doping with lithium or zinc ions was used. The results are presented in Table 1.

TABLE 1

| Catalyst | Unconverted Acetone, % | Mesityl Oxide, % | Isophorone % | Other Products, % |
| --- | --- | --- | --- | --- |
| Control A | 10.0 | 0.8 | 31.5 | 57.7 (1) |
| Example 1 | 8.9 | 1.9 | 40.0 | 49.2 (2) |

TABLE 1-continued

| Catalyst | Unconverted Acetone, % | Mesityl Oxide, % | Isophorone % | Other Products, % |
| --- | --- | --- | --- | --- |
| Example 2 | 16.6 | 1.4 | 33.2 | 48.8 (2) |

(1) 39% 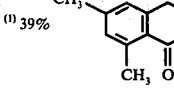 + unknown products 3,3,6,8-tetramethyltetralone-1

(2) 33.9% 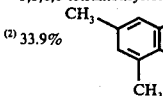 + unknown products 3,3,6,8-tetramethyltetralone-1

EXAMPLE 4

Pilot Plant Reactor Evaluation of Lithium Ion Doped Catalysts

Acetone (99% pure) was fed to the 1 inch × 10 foot pilot plant reactor described supra which was packed with a ⅛ inch pelleted, lithium doped catalyst prepared as in Example 1. The elemental analysis of this catalyst indicated the following composition:

C, 2.41% (due to a graphite lubricant for pelleting)
Al, 3.49%
Mg, 47.47%
S, 0.03%
Cl, 0.32%
Li, 0.05%

This catalyst had the following physical properties:

| Pellet crush strength | 6 lbs. |
| --- | --- |
| Pore volume | 0.32 cc./g. |
| Surface area (After heating to 350° C.) | 115 m²/g. |
| Bulk density | 0.86 g./cc. |

The feed rate of the acetone above was 44 lbs./ft.³ of catalyst/hr. at 300° C./40 psi.

About 18.4% of the acetone was converted into isophorone and mesityl oxide at an efficiency of 85.4%. The concentration of mesityl oxide and isophorone in the product stream was 5.6 and 7.8% respectively, representing a mesityl oxide/isophorone product ratio of 0.72. These data are delineated in Table 2 along with six other runs made at different operating conditions of feed rate and pressure with temperature held constant at 300° C.

TABLE 2

| | 1" × 10' PILOT PLANT REACTOR RESULTS | | | | |
| --- | --- | --- | --- | --- | --- |
| Mesityl Oxide (wt. %) | Isophorone (wt. %) | Mesityl Oxide Isophorone (wt. %) | Total Acetone Conversion (%) | Efficiency to Mesityl Oxide + Isophorone (%) | Operating Conditions (° C)/psi/lbs. |
| 5.6 | 7.8 | .72 | 18.4 | 85.4 | 300/40/44 |
| 5.6 | 10.9 | .5 | 23.8 | 81.7 | 300/40/22 |
| 5.0 | 5.0 | 1.0 | 13.8 | 84.8 | 300/40/66 |
| 4.4 | 3.8 | 1.9 | 10.2 | 94.2 | 300/40/132 |
| 4.8 | 19.6 | .24 | 36.8 | 76.4 | 350/40/22 |
| 6.2 | 9.0 | .71 | 21.4 | 87.3 | 300/40/44 |
| 3.9 | 7.0 | .55 | 15.6 | 81.4 | 300/0/44 |

EXAMPLE 5

An Alternate Lithium Ion Doped Catalyst Preparation

To a solution of 149 g. of magnesium nitrate, $Mg(NO_3)_2 \cdot 6H_2O$, in 1 liter of distilled water was added over a 30 minute period with stirring a solution of 42.1 g. of sodium hydroxide in 400 ml. of distilled water. A white precipitate appeared at once which was slurried in the aqueous medium. To this slurry was added a solution of 3.2 g. of sodium aluminate, NaAlO$_2$, in 110 ml. of distilled water. The pH after the addition of the sodium aluminate was complete was 8–9. After standing overnight the reaction mixture was filtered and the filter cake washed with three 500 ml portions of distilled water. The filter cake was contacted overnight with 500 ml of water in which 0.1 g. of lithium nitrate, LiNO$_3$ had been dissolved. The slurry which resulted was filtered and the filter cake dried at 100° C. for 18 hours under a vacuum of 30 mm Hg. The yield of white solid catalyst was 29.3 grams.

EXAMPLE 6

Lithium Ion Doped Catalyst Preparation

To 149 g. of Mg(NO$_3$)$_2$.6H$_2$O in one liter of distilled water was addd a solution of 42.1 g. of NaOH, 3.2 g. of NaAlO$_2$ in 500 ml. of distilled water slowly over a period of 30 minutes. A precipitate appeared at once and the pH at the end of the addition was 8–9. The precipitate was filtered and washed three times with 500 ml of distilled water. The precipitate was then contacted with a solution consisting of 0.1 grams of LiNO$_3$ in 500 ml of distilled water. The so-treated precipitate was dried at 100° C. for 18 hours under a vacuum of 30 mm Hg. The dried catalyst amounted to 31.8 grams.

EXAMPLE 7

Lithium Ion Doped Catalyst Preparation

To a solution of 140 grams of Mg(NO$_3$)$_2$.6H$_2$O and 15.3 grams of Al(NO$_3$)$_2$.9H$_2$O in one liter of distilled water was added a solution of 43.7 grams of NaOH in 500 ml of distilled water slowly over a 30 minute period with stirring. The pH at the end of the addition was 8–9. The precipitate which appeared was filtered and washed three times with 500 ml portions of distilled water. The filter cake was redispersed in 500 ml of distilled water containing 0.1 grams of LiNO$_3$ and left to stand overnight. It was then filtered, dried at 100° C. for 18 hours under a vacuum of 30 mm Hg. The yield of dry catalyst was 29.0 grams.

EXAMPLE 8

Lithium Ion Doped Catalyst Preparation

To a solution of 43.7 grams of NaOH in 500 ml. of distilled water was added a solution of 149 g. of Mg(NO$_3$)$_2$.6H$_2$O and 15.3 grams of Al(NO$_3$)$_3$.9H$_2$O in 1 liter of distilled water slowly over a 30 minute period with good stirring. At the end of this time the pH of the mixture was 8–9. The precipitate which formed was filtered and washed three times with 500 ml. portions of distilled water. The filter cake was redispersed in 500 ml. of distilled water containing 0.1 g. of LiNO$_3$. The product was filtered and dried at 100° C. for 18 hours under a vacuum of 30 mm Hg. The yield of catalyst was 30.9 grams.

EXAMPLE 9

Catalyst Evaluations

The catalyst preparation described in Examples 5, 6, 7 and 8 were evaluated in the pulse-gas chromatographic technique described supra using two micro liters of acetone as the active hydrogen containing organic carbonyl compound. The results are delineated in Table 3.

EXAMPLE 10

Pilot Plant Reactor Evaluation of Lithium Ion Doped Catalysts with Aliphatic Aldehydes The pilot plant reactor described in Example 4 was packed with 1091 g. of the catalyst which was described in Example 1. The particles were sized to a diameter of 0.4–2.4 millimeters. The reactor was heated to 280° C. at a pressure of 40 psig while pumping at 50:50 (weight) mixture of n-butyraldehyde and isobutyraldehyde at a rate of about 700 grams per hour. Gas chromatographic analysis and material balance shows the following results:

Percent in n-butyraldehyde reacted = 51.0
Percent isobutyraldehyde reacted = 6.0

TABLE 3

| CATALYST | UNCONVERTED ACETONE, % | MESITYL OXIDE WT. | ISOPHORONE, % | OTHER PRODUCTS | |
|---|---|---|---|---|---|
| | | | | ISOXYLITONES[a] | TETRALONES[b] |
| Exp. 5 | 18.2 | 3.3 | 32.3 | 5.6 | 36.6 |
| 6 | 57.7 | 6.4 | 31.0 | 0.8 | 2.7 |
| 7 | 27.1 | 2.6 | 39.8 | 2.7 | 17.6 |
| 8 | 77.9 | 13.8 | 5.1 | 0 | 0 |

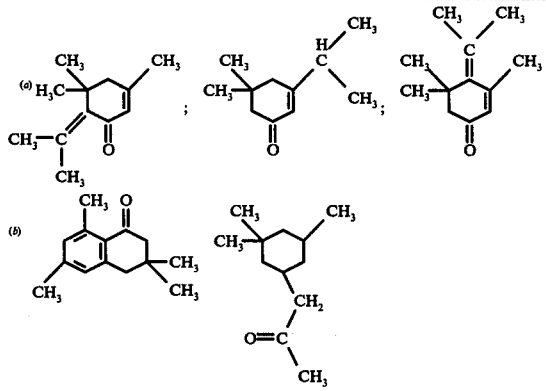

The efficiency of the catalyst evaluated herein depends upon the specificity with which n-butyraldehyde condensed with itself to form 2-ethylhexenealdehyde rather than with isobutyraldehyde to form a corresponding isomer. It was found that the efficiency of the former reaction to form 2-ethylhexenealdehyde was 65.9 percent as opposed to an efficiency of 11.0 percent for the condensation of n-butyraldehyde with isobutyraldehyde to form that dimer. The efficiency of forming a trimmer of 3 n-butyraldehyde units was 19.6 percent. Therefore the total reaction efficiency was 93.8 percent. This evaluation demonstrates that the catalyst evaluated herein discriminates in favor if an n-butyraldehyde plus n-butyraldehyde condensation in preference to isobutyraldehyde plus n-butyraldehyde or isobutyraldehyde plug isobutyraldehyde condensation by almost an order to magnitude.

EXAMPLE 11

Evaluation of Lithium Ion Doped Catalysts with Anhydrous Acetaldehyde

The lithium doped catalyst described in Example 1 was shaped into ⅛ inch pellets and 145 grams packed into a stainless steel pipe reactor having the dimensions 1 × 12 inches followed by a condenser and receiver. At 40 psi and 280° C. about 90 grams per hour of anhydrous acid acetaldehyde was pumped through this arrangement. Gas chromatographic analysis showed that 67.2 percent of acetaldehyde was recovered, 25.6 percent of the dimer

was produced and 7.2 percent of the trimer

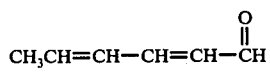

was produced.

EXAMPLE 12

Evaluation of Lithium Doped Catalyst with Cyclohexanone

Using the equipment described in Example 11, ninety grams per hour of cyclohexanone feed was passed through the reactor at 40 psi and 280° C. Gas chromatographic analysis showed the product consisted of 85.3 percent of cyclohexanone and 12.3 percent of a mixture of dimers having the structural formulae shown below:

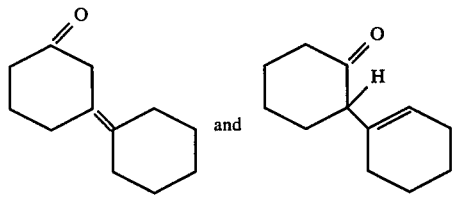

Although the invention has been described in its preferred forms with a certain degree of particularity, it is understood that the present invention disclosure has been made only by way of example and that numerous changes can be made without departing from the spirit and the scope of the invention.

What is claimed is:

1. Catalyst prepared by the steps of:
   (a) interacting stoichiometric amounts of a water-soluble salt of a metal of Group II of the Deming Periodic Table and a water-soluble aluminum salt with a stoichiometric amount of an alkali metal or alkaline earth metal, water-soluble hydroxide in water to precipitate a water-insoluble slurry of mixed hydroxides, with the proviso that the ratio of gram atoms of Group II metal to aluminum metal is in the range of about 0.02 to about 0.3;
   (b) washing the slurry from step (a) with water until substantially free of water-soluble salt;
   (c) contacting the washed slurry from step (b) with a dilute aqueous solution of a lithium or a zinc salt at ambient temperature; and
   (d) recovering and drying the product of step (c) at a temperature below about 400° C.

2. Catalyst claimed in claim 1 wherein the Group II metal salt is magnesium nitrate and the hydroxide is an alkali metal hydroxide.

3. Catalyst claimed in claim 1 wherein 100 parts by weight of the product from step (c) contains from about 1.0 to about 0.001 parts by lithium or zinc ion.

4. Catalyst claimed in claim 1 wherein the washed slurry from step (b) is contacted with an aqueous solution which contains about 1 to about 3 percent by weight of a water soluble lithium salt in step (c).

5. Catalyst claimed in claim 4 wherein the lithium salt is a lithium halide.

6. Catalyst claimed in claim 5 wherein the lithium halide is lithium chloride.

7. Catalyst claimed in claim 1 wherein the washed slurry from step (b) is contacted with an aqueous solution which contains about 1 to about 3 percent by weight of a zinc salt in step (c).

8. Catalyst claimed in claim 7 wherein the zinc salt is a zinc halide.

9. Catalyst claimed in claim 8 wherein the halide is zinc chloride.

10. Catalyst claimed in claim 1 wherein the aluminum salt is aluminum nitrate and the hydroxide is an alkali metal hydroxide.

11. Catalyst claimed in claim 1 wherein the aluminum salt is an alkali metal aluminate.

12. Catalyst prepared by the steps of:
    (a) interacting a stoichiometric amount of a water-soluble salt of a metal of Group II of the Deming Periodic Table with a stoichiometric amount of an alkali metal or alkaline earth metal water-soluble hydroxide in water to precipitate a water insoluble slurry;
    (b) mixing 100 parts by weight on a dry basis of the slurry of step (a) with about 1 to about 20 parts by weight of a water-soluble salt of a metal of Group II of the Deming Periodic Table dissolved in water to produce a second slurry;
    (c) mixing 100 parts by weight on a dry basis of the slurry of step (b) with about 2 to about 40 parts by weight on a dry basis of an alkali metal aluminate to afford a third slurry; p1 (d) washing the slurry of step (c) with water until substantially free of water soluble salts;
    (e) contacting the washed slurry of step (d) with a dilute aqueous solution of a lithium or zinc salt at ambient temperature; and
    (f) recovering and drying the product of step (e) at a temperature below about 400° C.

13. Catalyst claimed in claim 12 wherein the Group II metal salt used in step (a) and (b) is magnesium nitrate and the hydroxide in step (a) is an alkali metal hydroxide.

14. Catalyst claimed in claim 12 wherein the ratio of Group II metal salt in step (b) to the alkali metal aluminate in step (c) is about 1:2±10 mole %.

15. Catalyst claimed in claim 12 wherein the slurry obtained from step (d) contains 80 to about 99 percent by weight of the precipitate from step (a) and about 1 to about 20 percent by weight of the slurry obtained in step (c).

16. Catalyst claimed in claim 15 wherein 100 parts by weight of the slurry from step (e) contains about 1.0 to about 0.001 parts by weight of lithium or zinc ion.

17. Catalyst claimed in claim 15 wherein the washed slurry of step (d) is contacted with an aqueous solution which contains about 1 to 3 percent by weight of a water-soluble lithium inorganic salt in step (c).

18. Catalyst claimed in claim 17 wherein lithium inorganic salt is a lithium halide.

19. Catalyst claimed in claim 18 wherein the lithium halide is lithium chloride.

20. Catalyst claimed in claim 12 wherein the washed slurry from step (d) is contacted with an aqueous solution containing about 1 to about 3 weight percent by weight of a zinc salt in step (c).

21. Catalyst claimed in claim 20 wherein the zinc salt is a zinc halide.

22. Catalyst claimed in claim 21 wherein the zinc halide is zinc chloride.

23. Catalyst claimed in claim 12 wherein the pore volume is about 0.2 to about 0.5 cc./g., the surface area about 20 to about 400 meters$^2$/g. and the bulk density is about 0.8 to about 0.9 cc./g.

* * * * *

UNITED STATES PATENT AND TRADEMARK OFFICE
CERTIFICATE OF CORRECTION

PATENT NO. : 4,086,188
DATED : April 25, 1978
INVENTOR(S) : Walter Thomas Reichle It is certified that error appears in the above-identified patent and that said Letters Patent are hereby corrected as shown below:

Col. 2, lines 12-14 delete the phrase "the ratio of gram atoms of Group II metal to aluminum metal is in the range of about 0.02 to about 0.3" and substitute therefor the phrase --the ratio of gram atoms of aluminum metal to Group II metal is in the range of about 0.02 to about 0.3--.

Col. 4, line 1 before "temperatures" the word "of" should read --to--.

Col. 6, line 1 the phrase "Readings were a" should be --Readings were on a--.

Col. 6, line 31 "catalyst from acetone" should read --catalyst for acetone--.

Col. 7, line 27 "of the wek cake" should read --of the wet cake--.

Col. 9, line 19 "water was addd" should read --water was added--.

UNITED STATES PATENT AND TRADEMARK OFFICE
CERTIFICATE OF CORRECTION

PATENT NO. : 4,086,188
DATED : April 25, 1978
INVENTOR(S) : Walter Thomas Reichle It is certified that error appears in the above-identified patent and that said Letters Patent are hereby corrected as shown below:

Col. 11, line 5 "trimmer" should read --trimer--.

Claim 1, lines 8-10 delete the phrase "the ratio of gram atoms of Group II metal to aluminum metal is in the range of about 0.02 to about 0.3" and substitute therefor the phrase --the ratio of gram atoms of aluminum metal to Group II metal is in the range of about 0.02 to about 0.3--.

Claim 3, line 3 "by lithium" should read --by weight of lithium--.

Claim 12, line 16 delete the symbol "pl" and start --(d) washing the slurry of step (c) with water until substantially free of water soluble salts;-- as a new paragraph.

Signed and Sealed this

Tenth Day of July 1979

[SEAL]

Attest:

LUTRELLE F. PARKER
Attesting Officer        Acting Commissioner of Patents and Trademarks